United States Patent [19]

Kusakabe et al.

[11] 4,234,691

[45] Nov. 18, 1980

[54] L-LYSINE α-OXIDASE

[75] Inventors: Hitoshi Kusakabe, Kyoto; Kenjiro Kodama, Choshi; Yuichiro Midorikawa, Choshi; Akira Kuninaka, Choshi; Haruo Misono, Hirakata; Kenji Soda, Uji, all of Japan

[73] Assignee: Yamasa Shoyu Kabushiki Kaisha, Chiba, Japan

[21] Appl. No.: 15,179

[22] Filed: Feb. 26, 1979

[30] Foreign Application Priority Data

Feb. 27, 1978 [JP] Japan .................................. 53/20993
Jun. 16, 1978 [JP] Japan .................................. 53/73441

[51] Int. Cl.$^2$ ............................................. C12N 9/06
[52] U.S. Cl. .................................... 435/191; 435/25; 435/945
[58] Field of Search .................... 195/62, 65; 435/191

[56] References Cited

PUBLICATIONS

Greenberg, ed., Metabolic Pathways, Third edition, vol. 3, pp. 38–47, (1969).
Glick, ed., Methods of Biochemical Analysis, vol. IV, pp. 285–306, (1957).
Analytical Biochemistry, vol. 49, pp. 225–239, (1972).
Analytical Biochemistry, vol. 87, pp. 283–286, (1978).
Guilbault, Handbook of Enzymatic Methods of Analysis, pp. 217–219, (1976).

*Primary Examiner*—Lionel M. Shapiro
*Attorney, Agent, or Firm*—Wenderoth, Lind & Ponack

[57] ABSTRACT

An L-lysine α-oxidase, that is, a novel L-amino acid oxidase having very high substrate-specificity to L-lysine is produced by culturing a specific microorganism belonging to Trichoderma in a medium.

6 Claims, 3 Drawing Figures

L-LYSINE α-OXIDASE

BACKGROUND OF THE INVENTION

1. Field of the Invention

This invention relates to a novel L-amino acid oxidase having very high substrate-specificity with respect to L-lysine, that is, an L-lysine α-oxidase.

This invention also relates to microbiological production of the L-lysine α-oxidase.

2. Description of the Prior Art

Hitherto there have been reports on the presence of L-amino acid oxidases in microorganisms, snake venom, the rat kidney, the fowl liver, and invertebrates (Arch Biochem, Biophys. Vol 146, p.p. 54–63, 1971; Journal of Bacteriology, Vol 121, No. 2, p.p. 656–662, February, 1975; and the Tanpakushitsu.Kakusan.Koso, Vol. 17, No. 1, p.p. 42–55, 1972). An L-amino acid oxidase having very high substrate-specificity to L-lysine has never been known in the art. In other words, known L-amino acid oxidases exhibit only very low enzyme activities to L-lysine except that an L-amino acid oxidase preparation derived from the turkey liver exhibits a high activity to L-lysine. However, the turkey liver enzyme also effectively oxidizes several amino acids other than L-lysine, such as L-arginine, L-histidine and L-ornithine. Thus, the oxidase preparation can not be considered to be an enzyme having especially high substrate-specificity to L-lysine.

As L-aminoacid-degrading enzymes having antitumor properly, L-asparaginase (the Tanpakushitsu.-Kakusan.Koso, Vol. 15, No. 5, p. 515, 1970); L-glutaminase (Nature, Vol. 227, p. 1136, 1970, and Science, Vol. 172, p. 732, 1971); L-phenylalanine ammonia-lyase (Cancer Res., Vol. 32, p. 285, 1972, and vol. 33, p. 2529, 1973); L-methionine γ-lyase (Cancer Res., Vol. 33, p. 1866, 1973); L-tyrosine phenol-lyase (Cancer Res., Vol. 36, p. 167, 1976), L-leucine dehydrogenase (FEBS Letters, Vol. 33, p. 286, 1973); threonine deaminase (Cancer Res., Vol. 37, p. 2523, 1977); and the like are known. There has been no report, however, that L-amino acid oxidases have antitumor property.

SUMMARY OF THE INVENTION

It is an object of this invention to provide an L-lysine α-oxidase, that is, an L-amino acid oxidase which has the capability of forming α-keto-ε-aminocaproic acid, ammonia and hydrogen peroxide via the oxidative deamination of L-lysine in the presence of water and oxygen with a very low Km value with respect to L-lysine and the high substrate-specificity to L-lysine.

Another object of this invention is to provide a process for the production of L-lysine α-oxidase which comprises culturing an L-lysine α-oxidase-producing strain belonging to the genus Trichoderma in a medium and isolating the L-lysine α-oxidase from the resulting culture.

DESCRIPTION OF THE INVENTION

Figure 1:
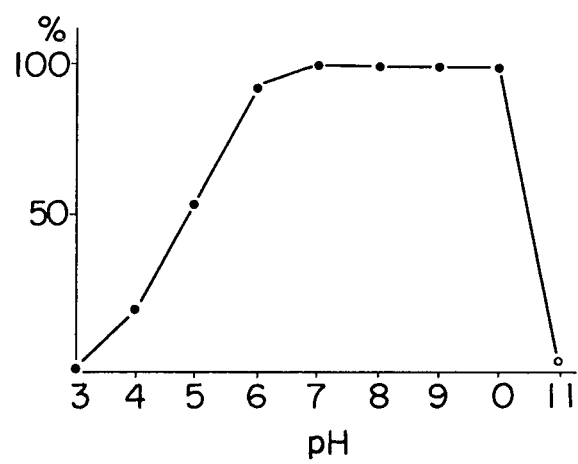
FIG. 1 is a graph of a curve indicating the pH stability of L-lysine α-oxidase.

I. Physical and Chemical Properties of L-lysine α-oxidases

The L-lysine α-oxidase of the present invention has a catalytic action and a substrate-specificity as described above. Its physical and chemical properties of the purified enzyme preparation which was produced and isolated according to the process for preparation thereof described in Example 1 are as follows.

(1) Enzymic action

The enzyme of the present invention deaminates oxidatively the α-amino groups of an L-amino acid in the presence of oxygen and produces an α-keto acid, ammonia and hydrogen peroxide, in the same manner as in the conventional L-amino acid oxidases but is a novel L-amino acid oxidase characterized by its very high substrate-specificity. When L-lysine is used as a substrate, one mol of L-lysine requires one mol each of oxygen and water to produce one mol of α-keto-ε-aminocaproic acid and one mol each of ammonia and hydrogen peroxide as shown in the following reaction formula.

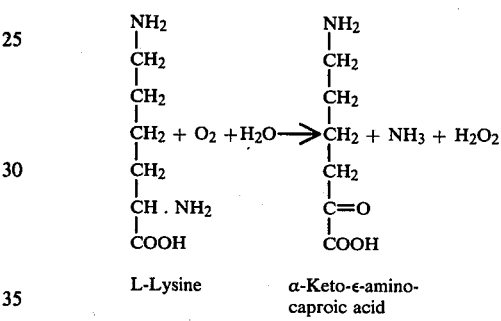

L-Lysine        α-Keto-ε-amino-
                caproic acid (2) Substrate specificity A variety of substrates listed in the following table were subjected to the action of the purified enzyme of the present invention, and the relative enzyme activities thereof were determined according to the oxygen-electrode method. As a result, the present enzyme showed a high substrate-specificity to L-lysine. In this connection, the enzyme of the present invention also showed some activities to L-ornithine, L-phenylalanine, L-histidine, and L-arginine. The affinity of the enzyme for each of these amino acids was much lower than that for L-lysine: the Km value of the enzyme for L-lysine was very low ($4 \times 10^{-5}$ M), whereas the values for L-ornithine and L-phenylalanine were $4.4 \times 10^{-4}$ M and $1.4 \times 10^{-2}$ M, respectively. The Km values for the other amino acids were considered to be as much as $1 \times 10^{-2}$ to $2 \times 10^{-2}$ M. Therefore, the enzyme of the present invention was found to be an L-amino acid oxidase which exhibits almost no action on the amino acids other than L-lysine when the concentration of the substrate was low, and to have a very high substrate-specificity to L-lysine. Thus, the present enzyme is referred to as L-lysine α-oxidase [E C 1, 4, 3; L-lysine: oxygen oxidoreductase (deaminating)].

| Substrate (10 mM) | Relative activity (%) | Substrate (10 mM) | Relative activity (%) |
|---|---|---|---|
| L-Lysine | 100.0 | L-Serine | <0.5 |
| L-Ornithine | 18.2 | L-Threonine | <0.5 |
| L-Phenylalanine | 8.3 | D-Lysine | <0.5 |

-continued

| Substrate (10 mM) | Relative activity (%) | Substrate (10 mM) | Relative activity (%) |
|---|---|---|---|
| L-Arginine | 6.1 | ε-Aminocaproic acid | <0.5 |
| L-Histidine | 3.8 | δ-Aminovareric acid | <0.5 |
| L-Asparagine | <0.5 | Putrescine | <0.5 |
| L-Glutamine | <0.5 | Cadaverine | <0.5 |
| L-Tryptophan | <0.5 | L-Citrulline | <0.5 |
| L-Methionine | <0.5 | Homocitrulline | <0.5 |
| L-Proline | <0.5 | 2,4-Diaminobutyric acid | <0.5 |
| L-Glutamic acid | <0.5 | α,β-Diaminopropionic acid | <0.5 |
| L-Aspartic acid | <0.5 | ε-N-Acetyl-L-lysine | <0.5 |
| L-Cysteine | <0.5 | D,L-Homolysine | 31.1 |
| L-Glycine | <0.5 | δ-Hydroxy-lysine | 37.1 |
| L-Alanine | <0.5 | L-Lysine hydroxamate | 62.1 |
| L-Hydroxyproline | <0.5 | L-Lysine ethyl ester | 83.3 |
| L-Leucine | <0.5 | S-(β-Aminoethyl)-L-cysteine | 9.8 |
| L-Isoleucine | <0.5 | S-(β-Aminopropyl-L-cysteine | 34.8 |
| L-Valine | <0.5 | S-(β-4-Pyridylethyl)-L-cysteine | 2.7 |

(3) Measurement of the enzyme activity

The activity of the present enzyme was measured in accordance with Soda's method (Analytical Biochemistry Vol. 25, p. 228, 1968) in the following manner. A reaction mixture consisting of 0.7 ml of 0.1 M potassium phosphate buffer (pH 8.0), 0.1 ml of catalase (750 U/ml), 0.1 ml of 0.1 M L-lysine solution and 0.1 ml of the present enzyme solution was incubated at 37° C. for 20 minutes with gentle shaking. After the incubation the reaction was terminated by the addition of 0.1 ml of 25% trichloroacetic acid. To the resulting reaction mixture were added 1.9 ml of 1 M acetate buffer (pH 5.0) and 0.8 ml of 0.1% 3-methyl-2-benzothiazolone hydrazone hydrochloride solution. The mixture was further incubated at 30° C. for 30 minutes and then allowed to cool to room temperature, after which measurement of optical density at 318 nm was carried out. The formed α-keto-ε-aminocaproic acid thus formed was determined from the resulting calibration curve. One unit of the enzyme was defined as the quantity of the enzyme catalyzing the formation of 1 μmol of α-keto-ε-aminocaproic acid at 37° C. per minute. The relative activity of the enzyme was also assayed by manometric and polarographic determination of the oxygen consumption.

(4) Optimum pH

The enzyme activity for L-lysine at various pH values was determined by using acetate buffers (pH5, pH6), phosphate buffers (pH6, pH7 and pH8), Tris-hydrochloric acid buffers (pH 7.5, pH 8.0, pH 8.5 and pH 9.0), and glycine-sodium hydroxide buffers (pH 9.0, pH 9.5 and pH 10.0). As a result, the optimum pH was found to be in the vicinity of 8 to 9.

(5) pH stability and thermal stability

After the enzyme was incubated at 45° C. for 20 minutes in the range of pH 3 to 11, and then the remaining enzyme activity was determined. The enzyme was found to be stable at the pH of 7 to 10 as shown in FIG. 1.

Figure 2:
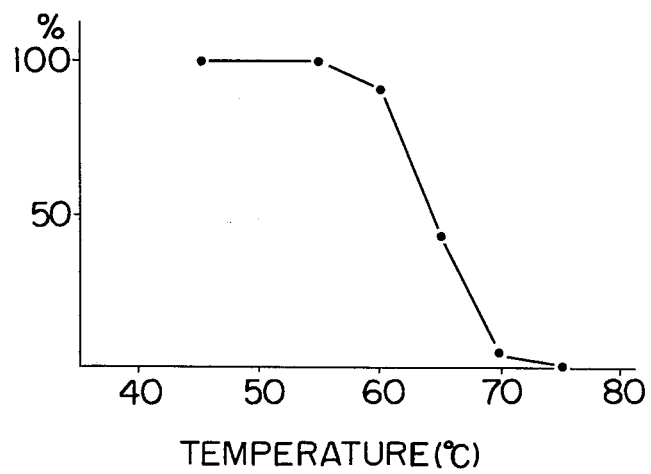
FIG. 2 is a graph of a curve indicating the thermal stability of L-lysine α-oxidase.

The thermal stability was also studied by incubation at pH 7.4 to 20 minutes at various temperatures, The enzyme was found to be stable at a temperature up to 55° C. as shown in FIG. 2.

(6) Optimum temperature

The enzyme activity was determined at various temperatures in 0.1 M potassium phosphate buffer (pH 7.4).

The optimum temperature of the present enzyme was observed to lie between 45° and 50° C.

(7) Inhibition, activation and stabilization

The enzyme activity was measured in the presence of various metallic ions and various additives. The enzyme was inhibited by copper ions, PCMB or mercuric chloride as shown in the following tables. The activator has not been found. The enzyme was stabilized by sodium chloride, potassium chloride, phosphates and the like.

| Metallic ions (1mM) | Relative activity (%) | Metallic ions (1mM) | Relative activity (%) |
|---|---|---|---|
| Zn | 92.7 | Ba | 100.0 |
| Co | 91.6 | Ca | 102.5 |
| Mn | 97.1 | Fe | 100.0 |
| Mg | 99.6 | Li | 98.4 |
| Cu | 78.5 | K | 100.0 |

| Inhibitors | Relative activity (%) |
|---|---|
| Cysteine | 100.3 |
| Glutathione | 103.5 |
| Tiron | 96.5 |
| N-Ethylmaleimide | 108.7 |
| EDTA | 93.8 |
| PCMB | 42.9 |
| Mercuric chloride | 19.2 |

Figure 3:
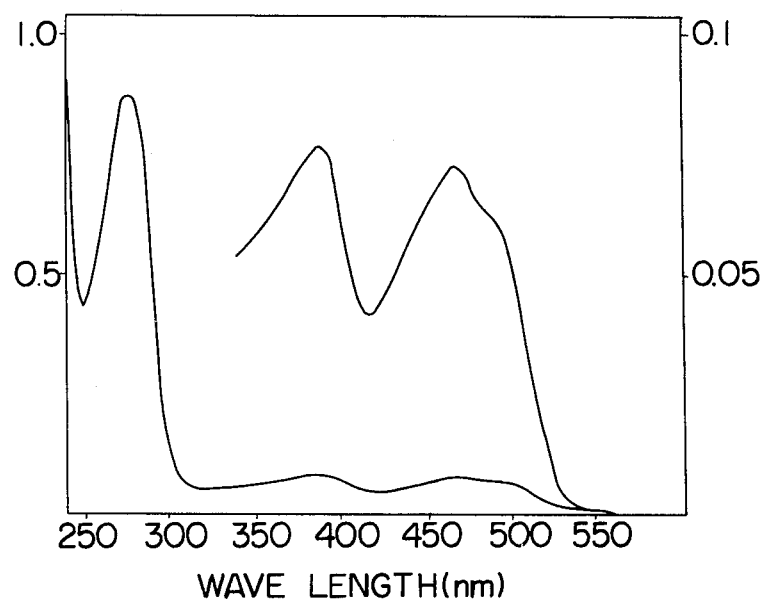
FIG. 3 is a graph indicating absorption spectrum.

(8) Absorption spectrum (FIG. 3)

$\lambda$max 277 nm ($\epsilon$247000); 388 nm ($\epsilon$24000); 466 nm ($\epsilon$22000).

$A_{1cm}^{1\%}$ at 280 nm 21.7

A 280/A 260 1.54

(9) Coenzyme

The present enzyme preparation was subjected to thermal or TCA treatment and then to centrifugation. The absorption spectrum of the resulting supernatant was in agreement with that of flavin adenine dinucleotide (FAD). Furthermore, the supernatant activated the apoenzyme of D-amino acid oxidase. Thus, the coenzyme of the present enzyme was found to be FAD. The coenzyme was also identified as FAD from the Rf value of thin-layer chromatography. It was confirmed that two moles of FAD was present in each mole of the present enzyme.

(10) Polyacrylamide gel electrophoresis and SDS-polyacrylamide gel electrophoresis—single band

(11) Isoelectric point—4.35

(12) Sedimentation constant—$S°_{20,w}$ 6.88

(13) Molecular weight

The molecular weight of the present enzyme was found to be 112,000 ($\pm$10,000) by a gel filtration method using Sephadex G-200. The present enzyme contains two identical subunits, the molecular weight of the subunit being 56,000 ($\pm$5,000) according to an electrophoresis method using SDS-polyacrylamide gel. The molecular weight of the enzyme was also determined to be 119,000 by an ultracentrifuge sedimentation equilibrium method.

(14) Analysis of amino acids

The following data were obtained from calculation on the basis that the subunit has a molecular weight of 56,000.

| Amino acids | Numbers of amino acid residues (mol amino acid/mol subunit) | | | Estimated numbers of amino acid residues |
|---|---|---|---|---|
| | 24 hrs. | 48 hrs. | 72 hrs. | |
| Lysine | 26.1 | 26.1 | 26.8 | 26 |
| Histidine | 11.8 | 11.4 | 11.6 | 12 |
| Arginine | 15.9 | 14.8 | 15.3 | 15 |
| Aspartic acid | 57.6 | 61.2 | 59.2 | 59 |
| Threonine | 27.1 | 28.3 | 27.2 | 28 |
| Serine | 25.1 | 25.3 | 23.5 | 25 |
| Glutamic acid | 42.2 | 45.5 | 44.5 | 44 |
| Proline | 22.5 | 21.6 | 25.5 | 23 |
| Glycine | 39.5 | 42.9 | 42.5 | 42 |
| Alanine | 35.6 | 38.2 | 37.1 | 37 |
| ½ Cystine | | | | 7 |
| Valine | 24.5 | 27.6 | 26.9 | 26 |
| Methionine | 11.8 | 10.6 | 10.4 | 11 |
| Isoleucine | 19.6 | 22.0 | 22.7 | 21 |
| Leucine | 42.6 | 45.6 | 45.5 | 45 |
| Thyrosine | 30.5 | 27.8 | 27.1 | 28 |
| Phenylalanine | 19.5 | 20.5 | 21.1 | 20 |
| Tryptophan | | | | 16 |

II Production of L-lysine α-oxidase

L-lysine α-oxidase can be produced by culturing a strain belonging to the genus Trichoderma and having the ability to form L-lysine α-oxidase in a medium and isolating it from the culture. The process for production of the present enzyme will now be described in detail.

A. Microorganisms to be used

The microorganisms to be used in the production of the present enzyme belong to the genus Trichoderma and have the ability to form L-lysine α-oxidase. Any strain having this fundamental properties can be used in the present invention, which includes newly-isolated strains found in nature, known cultured strains, and mutant strains having high ability to produce L-lysine α-oxidase which have been obtained by conventional artificial mutation methods, for example, physical treatments such as irradiation with ultraviolet rays, X-rays or γ-rays, and chemical treatments with nitrosoguanidine and the like. The process of the present invention utilizes basically the ability to synthesize L-lysine α-oxidase protein under the direction of the genes of Trichoderma microorganisms. Thus, in the present invention, the gene-recombined microorganisms can also be utilized. In such microorganisms, the genes of Trichoderma microorganisms concerned with the production of L-lysine α-oxidase have been combined with the bodies of other suitable microorganisms, for example, by the cell-fusion method using protoplast.

The novel strain, *Trichoderma viride* Y244-2-90 which was isolated from the soil collected at Mt. Mitsumine, Saitama, Japan by the present inventors has an especially high ability to produce L-lysineα-oxidase. Accordingly, in the practice of the present invention, strains of *Trichoderma viride* such as *Trichoderma viride* Y244-2-90 and its mutants can be used suitably.

The above-mentioned strain was deposited on Oct. 7, 1977 with FERMENTATION RESEARCH INSTITUTE, AGENCY OF INDUSTRIAL SCIENCE and TECHNOLOGY, Inage, Chiba City, Japan under term-P No. 4256. The strain was also deposited on Dec. 29, 1978 with the AMERICAN TYPE CULTURE COLLECTION (ATCC), 12301 Parklawn Drive, Rockville, Maryland, U.S.A. under ATCC No. 20536. Further, the strain of FERM-P No. 4256 was sent directly from the FERMENTATION RESEARCH INSTITUTE, AGENCY OF INDUSTRIAL SCIENCE AND TECHNOLOGY to the AMERICAN TYPE CULTURE COLLECTION for deposition, and deposited with ATCC On Jan. 30, 1979 under ATCC No. 20,538.

The taxonomical properties of the above-mentioned strain are given below.

(1) Growth on culture mediums

The above-mentioned strain was inoculated on the agar mediums given below and allowed to form giant colonies. The results of observation with the naked eye are shown in the following table.

| Mediums | State of colonies | Colors of reverse | Formation of conidia |
|---|---|---|---|
| Malt extract glucose agar medium | Hyphae are white and long, and grow thinly on the agar medium. Good growth | Colorless | Deep green conidia form on the peripheral region. |
| Czapek's agar medium | Hyphae are white and long, and grow very thinly on the agar medium. Inferior growth. | Colorless | Deep green conidia form thinly on the peripheral region. |
| Synthetic Mucor agar medium | Hyphae are white, long and felt-like. Good growth | Colorless | Deep green conidia form on the whole surface except the central region. |
| YpSs agar medium | Hyphae are white, long and felt-like. Good growth | Brownish | Deep green conidia form very thickly except the central region. |

(2) Morphological features

The morphological features of the present strain which was cultured on a malt extract agar medium are shown in the following table, in comparison with those of *Trichoderma viride* IFO 4847 used as the control microorganism.

| Organs | Strains | |
|---|---|---|
| | *Trichoderma viride* Y244-2-90 | *Trichoderma viride* IFO 4847 |
| Conidia lumps | 6 to 8μ | .7μ |
| Conidia | 2 to 3μ (sphere) | 3 to 4 × 3 to 8μ (spheroid) |
| Sterigmata | 2 to 3 × 8 to 10μ | 2 to 3 × 6 to 10μ |
| Branches of sterigmata | 2 to 3 | 2 to 3 |
| Conidiophores | 2 to 3μ | 2.5 to 3μ |
| Diameter of hyphae | 3 to 4μ | 3 to 4μ |

By microscopic observation, the present strain was found to have unicellular green conidia formed massively at the tops of short verticillately-branched sterigmata. The types of the organs of the present strain are similar to those of *Trichoderma viride* IFO 4847. So far as the present inventors are aware, the IFO 4847 is one of the strains most closely resembling the present strain; however, they differ in the shapes of the conidia, the degrees of insertions of conidia, and some other features.

(3) Physiological properties (a) Assimilation of carbon source

The present strain was cultured with shaking at 28° C. for 6 days in the Czapeck's medium into which 2 to 3% of the following compound had been added as a sole assimilable carbon source. The state of growth is shown in the following table.

| Type of the carbon source | Degree of growth |
|---|---|
| glucose, maltose, arabinose, D-xylose, mannose, fructose, galactose, lactose, rhamnose, soluble starch | good growth |
| sucrose, raffinose, inulin | poor growth |

(b) Assimilation of nitrogen source

The present strain was cultured with shaking at 28° C. for 7 days in the Czapeck's medium into which 1% of the following compound has been added as a sole assimilable nitrogen source. The state of growth is shown in the following table.

| Type of nitrogen source | Degree of growth |
|---|---|
| sodium nitrate | good growth |
| gelatin, peptone, ammonium nitrate, ammonium sulphate, potassium nitrate, ammonium chloride | poor growth |

(c) pH for growth

The present strain was cultured with shaking at 28° C. for 6 days in the YpSs medium whose pH had been adjusted as follows. The state of growth is shown in the following table.

| pH | 2 | 4 | 6 | 8 | 10 |
|---|---|---|---|---|---|
| State of growth | fair | good | good | good | poor |

(d) Temperature for growth

When the present strain was cultured in the YpSs medium with shaking, its growth was good at 20° to 28° C. and poor at 37° C.

The present strain was classified from the above-mentioned mycological properties and especially from its morphological properties. The strain was identified to belong to class of *Fungi Imperfecti*, sub-class of Deutromycetes, order of Moniliales, family of Moniliaceae, genus of Trichoderma and to be one of strains of Trichoderma viride, in accordance with "Ainsworth and Bisby's Dictionary of Fungi, 5th ed. (1961)" by G. C. Ainsworth.

B. Methods and Conditions for Culture

The methods and conditions of culturing microorganisms to produce L-lysine α-oxidase are not especially restricted provided they are not counter to the achievement of the objects of the present invention. In other words, methods and conditions which provide the environment capable of culturing productive microorganisms and producing L-lysine α-oxidase can be used.

From the present inventors' researches on the wild strain *Trichoderma viride* Y244-2-90, it has been found that the production of L-lysine α-oxidase with the present strain can be carried out more advantageously in solid mediums than in liquid mediums. The strain suitable for liquid-medium culture methods, however, can be obtained by strain-improvement techniques. Therefore, the standard methods and conditions for culture in the production of L-lysine oxidase by using a wild strain Y244-2-90 are shown herein and, of course, these methods and conditions may be suitably modified according to the types and properties of the microorganisms to be used.

Examples of solid mediums which can be used in a solid-medium culture method include the so-called wheat bran mediums prepared by spraying 60 to 80% by weight of water onto a commercial wheat bran, and natural cereal mediums containing rice, rice bran, corn and the like; mediums prepared by adding to the above-mentioned medium suitable amounts of a carbon source (e.g., glucose, glycerol, maltose, soluble starch, ethanol, etc.), a nitrogen source (amino acids, peptone, soy bean powder, protein hydrolyzates, corn steep liquor, meat extract, yeast extract, sodium nitrate, etc.), and minor components (sodium salts, potassium salts, manganese salts, calcium salts, zinc salts, phosphates, sulphates, etc.), which can be assimilated by the present strain; and mediums prepared by mixing these mediums in suitable compositions and granulating the mixture into suitable sizes and shapes.

The conditions for culture are a temperature of 20° to 30° C., a pH range of 4 to 8, and a period of 3 to 25 days.

In liquid-medium culture methods, it is possible to employ a variety of selections and formulations of carbon sources, nitrogen sources and minor components which can be assimilated by the present strain. For example, it has been confirmed that L-lysine α-oxidase can be produced by aerobic cultures employing a malt extract medium (malt extract 2%, glucose 2%, peptone 0.1%), a Saburaud's medium (maltose 4%, peptone 1%), a YpSs medium (soluble starch 1.5%, yeast extract 0.4%, dipotassium phosphate 0.1%, magnesium sulphate heptahydrate of 0.05%), or a sporulation medium (glucose 1.5%, Casamino acid 0.5%, malt extract 0.1%, yeast extract 0.1%, glycerol 1%). The culture is preferably carried out under a sufficient supply of oxygen in any medium. Thus, a shaking culture method and an aerated-agitation culture method are generally employed. The other conditions for culture are similar to those of solid medium culture methods.

It has been found that the present process for production of L-lysine α-oxidase can be carried out most efficiently in the following manner. *Trichoderma viride* Y244-2-90 or its artificial mutant strain is employed as the microorganism to produce L-lysine α-oxidase. When the *Trichoderma viride* Y244-2-90 is employed, the strain is cultured in a wheat bran medium humidized with 70% by weight of water at 28° C. for 14 days, and the resulting culture product is subjected to extraction with water to obtain a crude extract of L-lysine α-oxidase. This mode of producing L-lysine α-oxidase will be further explained in detail in Example 1. Changes and modifications of the embodiments of the invention such as in scale size can be optionally made, and the present invention should not be restricted by these embodiments and examples thereof.

C. Preparation and purification of L-lysine α-oxidase

L-lysine α-oxidase can be produced by culturing the microorganisms capable of producing the oxidase as described above. The forms of preparation as the enzyme preparations should be employed optionally in accordance with the uses of the enzyme preparations. The preparations may be in the form whose L-lysine α-oxidation activity can be utilized practically and in the form of fungous cells separated from the culture, treated fungous cells, culture liquids, culture filtrates, culture extracts, partly-purified enzyme solution or powder, purified enzyme powder or solution and the like.

In order to isolate L-lysine α-oxidase, the fungous cells may be collected from the culture, and L-lysine α-oxidase may be extracted with a suitable buffer solution, under ultrasonic treatment or a mechanical milling.

The present enzyme, however, can be efficiently collected directly from the liquid culture or the water-extract of solid culture since the enzyme is readily secreted out of the fungous cells. The purified preparation of L-lysine α-oxidase which is electrophoretically pure can be obtained from the resulting crude enzyme solution by conventional methods such as, dialysis method, salting out with ammonium sulphate, etc., precipitation with organic solvents such as ethanol and acetone, ion-exchange chromatography such as DEAE-cellulose chromatography and DEAE-Sephadex chromatography, adsorption chromatography such as hydroxy apatite chromatography, and gel filtration method using Sephadex G-200 and the like.

III Utility of L-lysine α-oxidase (1) Antitumor activity

The purified preparation of the present enzyme obtained in the example given below exhibited complete inhibition of proliferation of the L5178 Y mouse leukemic cells in vitro at a concentration of 3.3 mU/ml, and in 50% inhibition of the proliferation at a concentration of 1 mU/ml.

In this experiment, the antitumor activity in vitro was determined by measuring the proliferation-inhibition activity against the cultured L5178 Y mouse leukemic cells. More specifically, 0.1 ml of the sample diluted with a phosphate-buffered saline (PBS) was added to 0.9 ml of the cultured L5178Y cell suspension ($10^5$ cells/ml) with the logarithmic growth phase. The mixture was incubated, at 37° C. for 48 hours in a carbon dioxide incubator, and then the number of the cells was measured by means of a microcell counter.

It was also confirmed that the enzyme activity of L-lysine α-oxidase and the antitumor activity are exhibited in parallel at each step of purification.

(2) Use of the present enzyme for the assay of L-lysine

The present enzyme is characterized by a very high substrate-specificity with respect to L-lysine. The specific assay of L-lysine can be accomplished by determining the quantity of α-keto-ε-aminocaproic acid produced from L-lysine by the enzyme, determining the quantity of hydrogen peroxide produced from L-lysine by the enzyme by determining the quantity of oxygen generated by the decomposition of the hydrogen peroxide with catalase, determining the quantity of the hydrogen peroxide by colorimetric determination with peroxidase, or determining the quantity of oxygen consumed during the enzymatic reaction by an oxygen electrode method in which the present enzyme has been fixed on a membrane. Thus, the present enzyme can be used for simple, sensitive and specific assay of L-lysine. Especially, it is useful for the determination of lysine contents in foods and beverages, and for the diagnosis of lysineurea, hyperlysinemia and the like.

(3) Others

The present enzyme is of importance to researches on L-lysine metabolism and can be used as a tool for biochemical researches. The enzyme is also expected to be a therapeutic medicine for hyperlysinemia. Moreover, it will be useful for preparation of low-lysine food for hyperlysinemia patients.

The present invention will be further described by way of the following non-limitative example thereof.

EXAMPLE 1 (production of enzyme)

In a 300-ml conical flask were charged 8g of wheat bran, 5 ml of water and 1g of rice hulls. The mixture was subjected to sterilization at 120° C. for 30 minutes to prepare a wheat-bran medium for seeding. The *Trichoderma viride* Y244-2-90 (FERM-P No. 4256 and ATCC No. 20536) was inoculated onto the wheat-bran medium and cultured at 28° C. for 7 days to prepare seed molds.

Into each of six 5-liter conical flasks were placed 200g of wheat bran and 140 ml of water. This step was followed by sterilization at 120° C. for 30 minutes to prepare a culture medium. The above-mentioned seed mold was inoculated under germ-free conditions on the media and cultured at 28° C. for 14 days. The resulting culture was immersed in 9 liters of water for 1 hour, filtered and then passed through "Super cell" (supplied by Johns-Manville) to obtain about 9 liters of crude enzyme solution. Ammonium sulfate was added to this crude enzyme solution in a quantity to reach 30% of the saturated concentration, whereupon insolubles were separated, and the insolubles were removed by centrifugation. Ammonium salfate was further added to the supernatant to reach 60% of the saturated concentration to produce a precipitate. The separated precipitate was then dissolved in 500 ml of 0.02 M potassium phosphate buffer (pH 7.4), and the resulting solution was subjected to dialysis overnight with the same buffer solution. The precipitate formed in the course of the dialysis treatment was removed by centrifugation, and the resulting supernatant was applied on a DEAE-cellulose column (3.5×27 cm) which had been equilibrated with the same buffer solution. The column was washed with the same buffer solution containing 0.15 M sodium chloride, and then the adsorbed enzyme was eluted with the same buffer solution containing 0.2 M sodium chloride. The eluted active fractions were collected, dialyzed and concentrated, and then subjected to gel filtration with "Sephadex G-200" column (2×140 cm). Active fractions were collected and ammonium sulfate was added thereto in an amount of 60% of the saturated concentration. The separated precipitate was collected by centrifugation and dissolved in 5 ml of 0.02 M Tris-hydrochloric buffer (pH 8.4) containing 0.1 M of sodium chloride. This step was followed by dialysis overnight with the same buffer solution.

The dialyzed internal solution was subjected to centrifugation. The resulting supernatent was applied on a DEAE-Sephadex A-50 column (0.7×4 cm), and the column was washed with 0.02 M Tris-hydrochloric acid buffer containing 0.15 M of sodium chloride. The adsorbed enzyme was then eluted with the same buffer solution containing 0.2 M of sodium chloride. Active fractions were collected and subjected to dialysis with 0.01 M potassium phosphate buffer. The dialyzed internal solution was subjected to centrifugation and the resulting supernatant was freeze-dried to obtain 18.4 mg of a purified preparation of L-lysine α-oxidase (yield 6.6%, specific activity 85.5 units/mg of protein).

The abbreviations used herein are as follows.

Km: Michaelis constant

NADH: Nicotinamide adenine dinucleotide reduced form

NADP: Nicotinamide adenine dinucleotide phosphate

NADPH: Nicotinamide adenine dinucleotide phosphate reduced form

PCMB: para-Chloromercuribenzoic acid

EDTA: Ethylenediaminetetraacetic acid

DEAE: Diethylaminoethyl

SDS: Sodium dodecyl sulfate

TCA: Trichloroacetic acid

IFO: Institute for Fermentation, Osaka (Japan)

What is claimed is:

1. L-lysine α-oxidase which is an L-amino acid oxidase having an ability to form α-keto-ε-aminocaproic acid, ammonia and hydrogen peroxide from L-lysine by oxidative deamination of L-lysine in the presence of water and oxygen as well as having a very low Km value with respect to L-lysine and the high substrate-specificity with respect to L-lysine.

2. The L-lysine α-oxidases as set forth in claim 1, in which the coenzyme thereof is flavin adenine dinucleotide.

3. The L-lysine α-oxidase as set forth in claim 1 or 2, in which the enzyme has a molecular weight represented by two subunits each having a molecular weight of 56,000 ($\pm$5,000) determined according to an electrophoresis method using SDS-polyacrylamide gel, a molecular weight of 112,000 ($\pm$10,000) determined according to a gel filtration method, and a molecular weight of about 119,000 determined according to ultracentrifuge sedimentation equilibrium method.

4. A process for production of L-lysine α-oxidase which comprises culturing a strain belonging to the genus of Trichoderma having an ability to produce L-lysine α-oxidase in a medium and isolating L-lysine α-oxidase from the resulting culture product.

5. The process as set forth in claim 4, in which the microorganism is of *Trichoderma viride*.

6. The process as set forth in claim 4, in which the microorganism is *Trichoderma viride* Y244-2-90 having an ATCC No. 20536 and FERM No. P4256.

* * * * *